Figure 1:
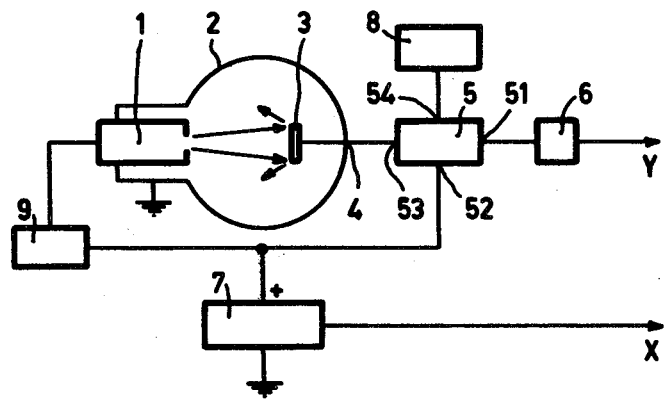

United States Patent [19]
Neave et al.

[11] 4,134,014
[45] * Jan. 9, 1979

[54] SPECTROSCOPY

[75] Inventors: James H. Neave, Horsham; Michael R. Boudry, London, both of England

[73] Assignee: U.S. Philips Corporation, New York, N.Y.

[*] Notice: The portion of the term of this patent subsequent to Nov. 9, 1994, has been disclaimed.

[21] Appl. No.: 468,278

[22] Filed: May 9, 1974

[30] Foreign Application Priority Data

May 23, 1973 [GB] United Kingdom ............... 24619/73

[51] Int. Cl.$^2$ ...................... H01K 37/26; H01J 39/00
[52] U.S. Cl. ..................................... 250/310; 250/305
[58] Field of Search ......................................... 250/310

[56] References Cited
U.S. PATENT DOCUMENTS

| | | | |
|---|---|---|---|
| 3,535,516 | 10/1970 | Munakata | 250/310 |
| 3,678,384 | 7/1972 | Oatley | 250/310 |
| 3,681,600 | 8/1972 | Rigden et al. | 250/310 |
| 3,736,422 | 5/1973 | Weber et al. | 250/311 |

OTHER PUBLICATIONS

"Voltage Measurement—Electron Probe" by J. P. Flemming, J. Physics E (G.B.) vol. 4, No. 10 (Oct. 1971).

*Primary Examiner*—Harold A. Dixon
*Attorney, Agent, or Firm*—Thomas A. Briody; Jack E. Haken

[57] ABSTRACT

A method of performing Auger electron spectroscopic surface analysis, e.g. of silicon, in which the secondary electrons which leave the target material are analyzed without the use of an electron optic device. An a.c. signal modulated retard potential is applied in ramp form to the target and a detection circuit connected to the target measures the component of current to earth from the target at the second harmonic of the a.c. modulation signal. The output of the detection circuit is plotted as a function of the retard potential to produce a spectrum of the first derivative of the secondary electron energy with respect to the retard potential so as to enhance the display of Auger transitions. Alternative realizations are described of a circuit arrangement including a four-port network for coupling the target, a.c. modulation signal source, retard potential source, and detector circuit.

5 Claims, 5 Drawing Figures

SPECTROSCOPY

This invention relates to spectroscopy, and in particular to methods of performing electron spectroscopic surface analysis of a solid material.

One such known method of surface analysis utilize characteristic Auger electron emission. If a primary electron beam of suitable energy is directed from a gun at a surface of a target of the material in a vacuum chamber, the energy spectrum of the secondary electrons will include certain fixed energy peaks which can be ascribed to electrons resulting from radiationless Auger transitions occurring in the target atoms and these peaks can be used to identify all elements except hydrogen and helium. In the Auger process a primary electron ejects another electron from a particular energy level in the target atom, and these two electrons can share the initial energy after scattering in any way which conserves the total energy of the system. However, when an electron from an energy level $E_2$ fills the vacancy created in level $E_1$, a fixed amount of energy $E_1-E_2$ is available to eject an electron from a third level $E_3$. This electron (an Auger electron) can appear outside the target with an energy $$E_4 = (E_1 - E_2) - (E_4 - E_3)$$

where $E_4$ is the value of the vacuum level. The Auger electrons produced by the primary beam have low energies (less than 2KeV), and very short mean free paths before energy loss, of the order to 10 Angstroms. The technique is thus extremely sensitive to surface conditions, and produces information about atoms in the top few atomic layers of the target.

Two methods are known for analyzing the secondary electrons so as to extract an energy spectrum, and they both use electron optic devices which must be contained in the vacuum chamber remote from the target.

In the retarding field method the electron optic device is typically a three-grid LEED system with a retard voltage applied to the second grid which is scanned from cathode potential to zero. A fluorescent screen behind the grids acts as the collector of the secondary electrons. A small a.c. modulating signal is superimposed on the retard voltage, and either the first or second harmonic of the a.c. component of the collected current is plotted against the retard voltage. The second harmonic is proportional to the second derivative of the collected current with respect to the retard potential which is proportional to the first derivative of the energy distribution of the secondary electrons. It is desirable to plot the first derivative of the energy distribution since this enhances the display in the spectrum of the Auger transitions which are superimposed on a background of secondary electrons of greater current.

In the electrostatic deflection method, the electron optic device is constituted by an electrostatic electron energy analyzer and electron multiplier. Electrons of known energy entering the entrance slit of the analyzer are refocussed at its exit slit for a particular voltage applied to the deflecting plates of the analyzer. Normal operation of the analyzer produces an energy distribution of the secondary electrons, and so if an a.c. modulating signal is superimposed on the swept deflection voltage, the first harmonic of the current collected by the electron multiplier is proportional to the first derivative of the secondary electrons.

Both the above-described known methods of analyzing the secondary electrons to obtain an Auger spectrum have two major disadvantages inherent in the use of an electron optic device. The overall sensitivity is limited because only that fraction of the secondary electrons leaving the target which is in the solid angle subtended by the electron optic device is collected. Also the physical size of the electron optic device limits the application of the technique to those cases where there is room for the electron optic device.

In fact, these two disadvantages inherent in the use of an electron optic device also supply more generally to the use of charge particle optical devices for energy analysis of a flux of charged particles in a vacuum chamber.

The object of the invention is to overcome these disadvantages.

According to the invention there is provided a method of performing energy analysis of a flux of charged particles emitted from a sample in a vacuum chamber, in which an a.c. signal modulated variable retard potential is applied to the sample, in which a detector circuit connected to the sample measures a current one separable component of which is proportional to the instantaneous net emitted flux of charged particles as a function of the retard potential, and in which said measured current as a function of the retard potential is used to produce an energy spectrum characteristic of the sample.

With particular reference to electron spectroscopy there is further provided, according to the invention, a method of performing electron spectroscopic surface analysis of a solid material, in which a primary electron beam is directed from a gun at a surface of a target of the material in a vacuum chamber, in which an a.c. signal modulated variable retard potential is applied to the target, in which a detector circuit connected to the target measures a current one separable component of which is proportional to all the secondary electrons which leave the target as a function of the retard potential, and in which said measured current as a function of the retard potential is used to produce an energy spectrum of said secondary electrons characteristic of the target surface.

In a preferred form of the electron spectroscopic method of this invention, the primary electron beam is of energy suitable for the production of Auger electron emission from the target surface, the detector circuit is tuned to measure the second harmonic of the a.c. modulation signal, and the detector output is plotted as a function of the retard potential to produce a spectrum of the first derivative of the secondary electron energy with respect to the retard potential so as to enhance the display of Auger transitions.

Thus whereas in the known methods of Auger electron spectroscopy electrons of all energies are allowed to leave the target surface simultaneously and a fraction of them are analysed by an electron optic device, in the method according to the invention only electrons of energy sufficient to overcome the swept retard potential leave the target surface and all these electrons are collected.

Because all of the secondary electrons that leave the target are analyzed by effectively performing the energy analysis at the target surface itself instead of using an electron-optic device, the overall sensitivity of the preferred method according to the invention is five times greater than the known retard potential method using an LEED electron optic device. At the same time the signal to noise ratio and resolution for Auger electrons are comparable with those of that known method.

Furthermore, because an electron-optic device is not used, the electron spectroscopic surface analysis method according to the invention is important because of its convenience and application to situations where electron-optic device analyzers cannot be included e.g., in-situ examination of contamination and ageing problems occurring in various types of electron tubes, application to surface chemistry and catalysis studies, substrate assessment in thin film growth studies, and direct incorporation in scanning electron microscopes and other similar instruments.

The electron spectroscopic method according to the invention requires the modulated retard potential to be applied to the target and a current indicative of all the secondary electrons which leave the target to be measured.

According to the invention there is further provided a circuit arrangement for use in this method, in which arrangement the input of said detector circuit is connected to the first port of a four port coupling network, the circuit arrangement being such that when the retard potential, the target and the a.c. modulation signal are connected to the second, third and fourth ports of the network respectively, then the retard potential is modulated and applied to the target and the a.c. current flowing in the target circuit produces an input current to the detector circuit.

A complete apparatus for performing the electron spectroscopic method according to the invention will include a vacuum chamber containing an electron gun, electrical power supplied to the gun, and usually means for holding the target in the chamber with electrical connection thereto. These component parts may already exist in known apparatus to which the invention can be applied, for example an electron spectrometer also used for electron spectroscopy other than Auger electron spectroscopy or a scanning electron microscope, and so these component parts as such form no part of the invention. A complete set of electrical apparatus which is specially adapted for performing the method of the invention will however include, according to the invention, the above-described circuit arrangement, a high voltage retard potential generator and an oscillator adapted to produce said a.c. modulation signal.

Figure 2:
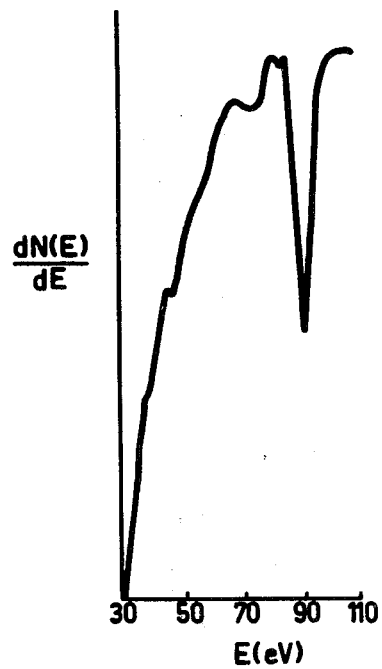
Figure 3:
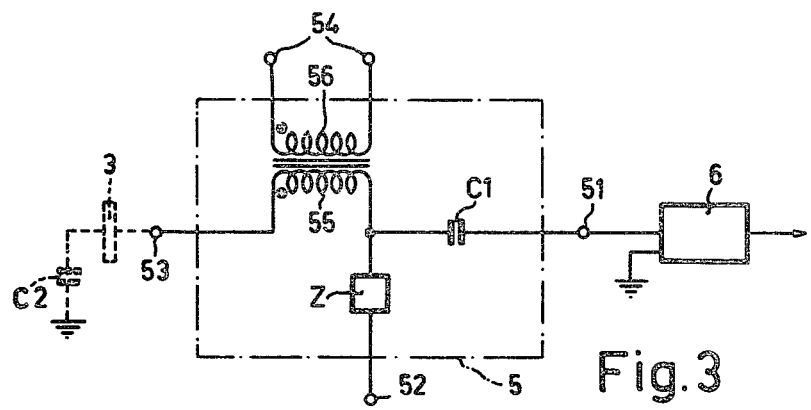
Figure 4:
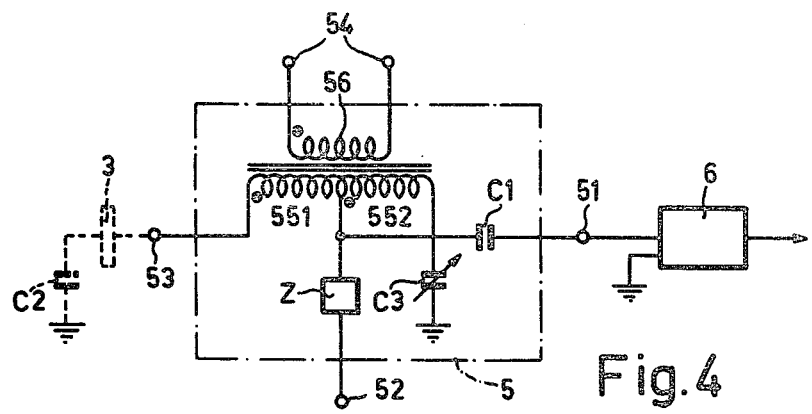
Figure 5:
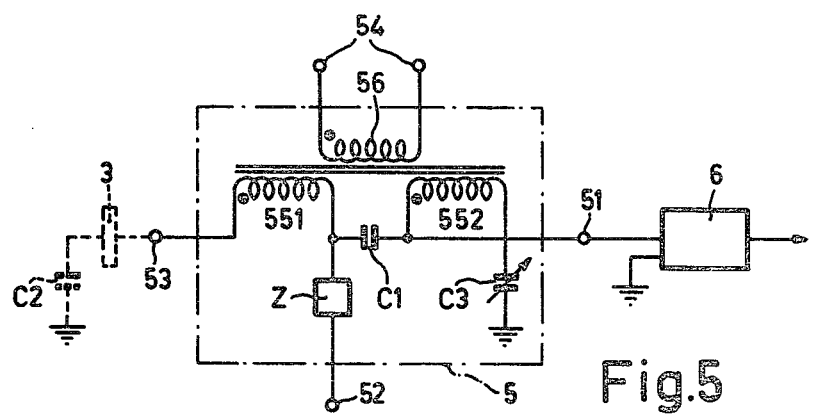

The invention will now be described in more detail with reference to the accompanying drawings, in which:

FIG. 1 shows a schematic diagram of apparatus for carrying out Auger electron spectroscopy according to the invention, FIG. 2 shows an Auger spectrum of silicon obtained by the method of the invention, and FIGS. 3, 4 and 5 show alternative realizations of a circuit arrangement according to the invention forming part of the apparatus shown in FIG. 1.

Referring now to FIG. 1, a primary electron beam, not necessarily focussed, of energy EeV is directed from an electron gun 1 in a vacuum chamber 2 at a surface of a target 3 of sample material. The surface of the target 3 is connected by an electrical feed-through 4 and a coupling network 5 to a frequency selective detector circuit 6 comprising a tuned amplifier followed by a phase-sensitive detector. A high voltage generator 7 produces a potential ramp, positive with respect to the earthed walls of the chamber 2, between zero and 2KeV. This potential ramp is applied to the surface of the target 3 via the circuit arrangement 5 where it is modulated by a 2KHz a.c. signal from an audio frequency oscillator 8. The potential ramp is also applied, unmodulated, to the electron gun power supplies 9 thus ensuring that the primary beam energy remains constant.

As the modulated potential ramp is applied to the target 3, electrons which have sufficient energy to overcome the potential barrier between the target 3 and the earthed walls of the chamber 2 will leave the target. The coupling network 5 passes to the detector circuit 6 a signal indicative of the current due to all the secondary electrons which leave the target 3 as a function of the retard potential. If the detector circuit 6 is tuned to the second harmonic of the a.c. modulation signal, then its output is proportional to the second derivative of the secondary electron current which is in turn proportional to the first derivative of the secondary electron energy. The output of the detector circuit 6 is applied to the Y input of an X—Y recorder (not shown), a voltage proportional to the output of the retard generator 7 is applied to the X input of the X—Y recorder, and the retard potential is scanned over the range of interest. The recorder thus produces a spectrum of the first derivative of the secondary electron energy, DN(E)/dE with respect to E, which is characteristic of the target surface. If the detector circuit 6 is tuned to the first harmonic of the a.c. modulation signal, then the recorder will produce a direct spectrum of the secondary electron energy, N(E) with respect to E.

FIG. 2 shows an Auger spectrum of the first derivative of the secondary electron energy of silicon obtained by the method above described with reference to FIG. 1. In this case a focussed primary electron beam of 2.25KeV energy and 1 λA current was used, and the modulating voltage was 2V r.m.s.

Some possible variations of the above-described method are as follows.

In the above-described method a particular primary electron beam energy of 2.25KeV has been used. There is no reason, e.g. if the technique is used in a scanning electron microscope, why beams of much higher energy (say 20 or even 50KeV) could not be used to produce Auger current. The reason for this is that the yield of Auger electrons as a function of primary beam energy reaches a maximum at somewhere between 3 to 20 times the level that it is desired to ionize; but one could exceed this amount by 50 or even 100 times, because the ionization cross-section for producing an Auger electron is fairly flat above the optimum value.

In the above-described method the potential ramp is applied unmodulated to the electron gun. On the one hand the a.c. modulation signal could also be applied to the electron gun. This would have the effect of removing from the plotted energy spectrum any peaks related directly to the energy of the primary electron beam, e.g. loss peaks. On the other hand it is also possible to perform the method of the invention without applying the potential ramp to the electron gun at all, particularly if a primary electron beam is used which strikes the surface of the target at normal incidence. If a glancing incidence electron gun is used, however, then there may be a variation in background signal level above a certain retard potential due, possibly, to electron diffraction effects which impair the performance. It then becomes more advantageous to ramp the gun supplies in order to keep the primary electron beam energy constant.

In the above-described method the retard potential is ramped. The method could alternatively be performed by varying the retard potential in a discontinuous manner.

Referring again to FIG. 1, the coupling network 5 may be considered as having four ports 51, 52, 53 and 54. In the operation of the methods described above, the detector circuit 6 is connected to the first port 51, the retarding potential ramp from the generator 7 is connected to the second port 52, the target 3 is connected to the third port 53 and the a.c. modulation signal from the oscillator 8 is connected to the fourth port 54.

The voltage at port 53 is the sum of the a.c. and d.c. signals on ports 54 and 52 respectively. The current flowing in the target circuit at port 53 comprises a d.c. component, an a.c. component at the drive frequency f of the oscillator 8 due to the target to ground stray capacitance and components due to secondary electron emission at the drive frequency f and its harmonics 2f, 3f etc. These last mentioned signals are proportional to the N(E), dN(E)/dE and higher derivative spectra respectively, and they must be separated from the other components either in the network 5 or in the detector 6. If dN(E)/dE spectra are to be plotted then frequency selection is sufficient to suppress the unwanted capacitance signal at frequency f. Suppression of this signal within the network 5 would be an advantage in that the design of the detector is less critical. If N(E) spectra, however, are required then the wanted signal is distinguished only by its phase from the unwanted capacitance signal; and since the magnitudes of these two signals may be very different, elimination of the larger capacitance signal in the network 5 is necessary.

A realization of the coupling network 5 which is suitable for dN(E)/dE spectra will now be described in more detail with reference to FIG. 3. In this network the first port 51 is connected via a capacitor C1 to one end of a secondary winding 55 of a transformer T1, the second port 52 of the network is connected via an impedance Z to the same end of the secondary winding 55, the third port 53 is connected to the other end of the secondary winding 55, and the fourth port 54 is connected to a primary winding 56 of the transformer T1.

The circuit arrangement of FIG. 3 ensures that the retard potential ramp applied to the target 3 via the port 52 is decoupled from the input of the detector circuit 6. The capacitor C1 blocks the d.c. retard potential ramp from the detector circuit 6 but has a low impedance at signal frequencies so that the detector 6 is connected to the transformer T1 at those frequencies. The impedance Z is high at the signal frequency so as not to shunt the signal into the source of retard potential, yet low at d.c. so as to avoid voltage drops associated with d.c. current in the target circuit. A further function of the impedance Z is to prevent components of noise at the signal frequency which are generated by the source of retard potential from being injected into the signal circuit.

The detector circuit 6 has a low input impedance at both the a.c. modulation signal frequency and at the detection frequency, i.e. the second harmonic of that frequency. It also has a well defined transfer characteristic relating the a.c. input current and the output quantity (normally a voltage) which is subsequently applied to the external recording device. One realization of the detector circuit 6 includes an operational amplifier around which is connected a feedback network which presents a high but well defined impedance at the detection frequency and a low impedance at the modulation frequency. In this case the e.m.f. induced in the secondary winding 55 by the a.c. modulation signal applied to the primary winding 56 appears substantially entirely on the target 3. The component at the second harmonic of the modulation frequency of the secondary electron currents in the target circuit flows directly through the secondary winding 55 into the detector circuit 6 provided the source of modulation voltage (i.e. the oscillator 8 shown in FIG. 1) has a low impedance at this higher frequency.

FIG. 4 shows an alternative realization of the coupling network 5, modified with respect to that shown in FIG. 3 so as to be suitable for producing N(E) spectra as well as being advantageous for dN(E)/dE spectra. The secondary winding of the transformer, now referenced T2, is split into two halves 551 and 552 with the half winding 552 connected to an adjustable capacitor C3.

The circuit arrangement of FIG. 4 ensures that while the a.c. signal applied to port 54 modulates the retard potential ramp applied to the target 3, it does not appear directly at the input of the detector 6. For the sake of explanation, the circuit arrangement of FIG. 4 may be considered as a bridge with the half windings 552 and 551 forming two arms; the opposite arms are formed by the target to earth capacitance C2 and the adjustable capacitor C3 which may be set to the same value as C2. The a.c. modulation signal applied to the port 54 and the detector circuit 6 are across opposite corners of the bridge. With the capacitor C3 correctly adjusted the signal applied to the port 54 produces equal and opposite current in the two half windings 552 and 551 which cancel at the input of the detector circuit 6. If, however, a current flows from the target 3 to earth due to secondary electrons leaving the target 3, then current will also flow at the input of the detector circuit 6. This circuit arrangement can be used to record either N(E) spectra or dN(E)/dE spectra. A change-over switch for these two modes of operation can be arranged which will either alter the drive frequency applied to port 54 or alter the amplifier tuned frequency and the phase sensitive detector reference channel within the frequency selective detector circuit 6.

FIG. 5 shows a variation of the circuit arrangement of FIG. 4. The neutralizing half 552 of the secondary winding of the transformer (now referenced T3) is separated from the other half 551 and is returned instead to the input of the detector circuit 6. This prevents application of the high retard potentials to the neutralizing capacitor C3. At the modulation signal and detection frequencies the operation of the circuit arrangement of FIG. 5 is the same as that of the circuit arrangement of FIG. 4.

What we claim is:

1. A method of performing electron spectroscopic surface analysis of a solid material, comprising the steps of directing a primary electron beam from a gun at a surface of a target of said material in a vacuum chamber, said primary electron beam being of energy suitable for the production of Auger electron emission from said target surface, applying an a.c. signal modulated variable retard potential to said target, providing a detector circuit connected to said target, said detector circuit is tuned to measure the second harmonic of the a.c. modulation signal, measuring with said detector circuit a current one separable component of said detector circuit being proportional to the instantaneous net emitted flux of secondary electrons which leave the target as a function of the retard potential, producing with said measured current as a function of the retard potential, an energy spectrum of said secondary electrons characteristic of the target surface and plotting the detector output as a function of the retard potential to produce a spectrum of the first derivative of the secondary electron energy with respect to the retard potential so as to enhance the display of Auger transitions.

2. A method as claimed in claim 1, in which the retard potential is applied in ramp form to the target, and in which the retard potential is also applied in ramp form to the gun so as to produce a substantially constant energy primary electron beam.

3. A circuit arrangement for use in the method as claimed in claim 1, in which arrangement the input of said detector circuit is connected to the first port of a four port coupling network, the circuit arrangement being such that when the retard potential, the target and the a.c. modulation signal are connected to the second, third and fourth ports of the network respectively, then the retard potential is modulated and applied to the target and the a.c. current flowing in the target circuit produces an input current to the detector circuit.

4. A circuit arrangement as claimed in claim 3, in which the four port network includes a transformer, and in which network the first port is connected via a capacitor to one end of a secondary winding of the transformer, the second portion is connected via an impedance to said one end of the secondary winding, the third port is connected to the other end of the secondary winding, and the fourth port is connected to a primary winding of the transformer.

5. A circuit arrangement as claimed in claim 4, in which a further secondary winding is provided on the transformer one end of which is connected to an adjustable capacitor and the other end is coupled to the detector circuit input, the arrangement being such that a.c. modulation signal produces equal and opposite currents through the two secondary windings which cancel at the detector circuit input.

* * * * *

UNITED STATES PATENT OFFICE
CERTIFICATE OF CORRECTION

Patent No. 4,134,014            Dated   January 9, 1979

Inventor(s) JAMES H. NEAVE ET AL

It is certified that error appears in the above-identified patent and that said Letters Patent are hereby corrected as shown below:

Delete claims 1—3 and substitute:

--1.    A method of performing energy analysis of a flux of charged particles emitted from a sample in a vacuum chamber, in which an a.c. signal modulated variable retard potential is applied to the sample, in which a detector circuit connected to the sample measures a current one separable component of which is proportional to the instantaneous net emitted flux of charged particles as a function of the retard potential, and in which said measured current as a function of the retard potential is used to produce an energy spectrum characteristic of the sample.

2.    A method of performing electron spectroscopic surface analysis of a solid material, in which a primary electron beam is directed from a gun at a surface of a target of the material in a vacuum chamber, in which an a.c. signal modulated variable retard potential is applied to the target, in which a detector circuit connected to the target measures a current one separable component of which is proportional to the instantaneous net emitted flux of secondary electrons which leave the target as a function of the

UNITED STATES PATENT OFFICE
CERTIFICATE OF CORRECTION

Patent No. 4,134,014  Dated January 9, 1979

Inventor(s) JAMES H. NEAVE ET AL

It is certified that error appears in the above-identified patent and that said Letters Patent are hereby corrected as shown below:

retard potential, and in which said measured current as a function of the retard potential is used to produce an energy spectrum of said secondary electrons characteristic of the target surface.

3. A method as claimed in Claim 2, in which the primary electron beam is of energy suitable for the production of Auger electron emission from the target surface, in which the detector circuit is tuned to measure the second harmonic of the a.c. modulation signal, and in which the detector output is plotted as a function of the retard potential to produce a spectrum of the first derivative of the secondary electron energy with respect to the retard potential so as to enhance the display of Auger transitions.--

Claim 4, line 1, "claimed in claim 3," should be --claimed in claim 7,--

Add claims 6—8 as follows:

--6. A method as claimed in Claim 2, in which the retard potential is applied in ramp form to the target, and in which the retard potential is also applied in ramp form to the gun so as to produce a substantially constant energy

UNITED STATES PATENT OFFICE
CERTIFICATE OF CORRECTION

Patent No. __4,134,014__  Dated __January 9, 1979__

Inventor(s) __JAMES H. NEAVE ET AL__

It is certified that error appears in the above-identified patent and that said Letters Patent are hereby corrected as shown below:

primary electron beam.

7. A circuit arrangement for use in the method as claimed in Claim 2, in which arrangement the input of said detector circuit is connected to the first port of a four port coupling network, the circuit arrangement being such that when the retard potential, the target and the a.c. modulation signal are connected to the second, third and fourth ports of the network respectively, then the retard potential is modulated and applied to the target and the a.c. current flowing in the target circuit produces an input current to the detector circuit.

8. A method of producing an energy spectrum characteristic of a surface, comprising the steps of:

bombarding the surface with a primary electron beam to liberate secondary electrons from the surface;

varying the voltage potential to the surface with respect to the surrounding space to variably retard seccondary electrons from leaving the surface;

modulating the varying voltage potential with an a.c. voltage signal; and measuring the a.c. component or a harmonic thereof

UNITED STATES PATENT OFFICE
CERTIFICATE OF CORRECTION

Patent No. 4,134,014           Dated January 9, 1979

Inventor(s) JAMES H. NEAVE ET AL

It is certified that error appears in the above-identified patent and that said Letters Patent are hereby corrected as shown below:

of the electrical current supplied to the surface as a function of the varying voltage potential to produce an energy spectrum characteristic of the surface.--

Signed and Sealed this

Twenty-fifth Day of September 1979

[SEAL]

*Attest:*

LUTRELLE F. PARKER
*Attesting Officer*     *Acting Commissioner of Patents and Trademarks*